US011819234B2

(12) United States Patent
Wood et al.

(10) Patent No.: US 11,819,234 B2
(45) Date of Patent: Nov. 21, 2023

(54) TISSUE RESECTING INSTRUMENT INCLUDING A ROTATION LOCK FEATURE

(71) Applicant: Covidien LP, Mansfield, MA (US)

(72) Inventors: Timothy J. Wood, Wilmington, MA (US); Peter F. Marshall, Bolton, MA (US)

(73) Assignee: Covidien LP, Mansfield, MA (US)

( * ) Notice: Subject to any disclaimer, the term of this patent is extended or adjusted under 35 U.S.C. 154(b) by 315 days.

(21) Appl. No.: 17/202,468

(22) Filed: Mar. 16, 2021

(65) Prior Publication Data

US 2021/0196304 A1 Jul. 1, 2021

Related U.S. Application Data

(63) Continuation of application No. 16/359,484, filed on Mar. 20, 2019, now Pat. No. 10,945,752.

(51) Int. Cl.
*A61B 17/32* (2006.01)
*A61B 17/42* (2006.01)

(52) U.S. Cl.
CPC .................. *A61B 17/32002* (2013.01); *A61B 2017/320024* (2013.01); *A61B 2017/4216* (2013.01); *A61B 2217/005* (2013.01); *A61B 2217/007* (2013.01)

(58) Field of Classification Search
CPC ............. A61B 17/320016–2017/32004; A61B 17/32002–2017/320032;
(Continued)

(56) References Cited

U.S. PATENT DOCUMENTS 1,585,934 A 5/1926 Muir
1,666,332 A 4/1928 Hirsch
(Continued)

FOREIGN PATENT DOCUMENTS

DE 3206381 A1 9/1983
DE 3339322 A1 5/1984
(Continued)

OTHER PUBLICATIONS

Extended European Search Report issued in corresponding European Application No. 20163429.2 dated Jul. 31, 2020, 9 pages.

*Primary Examiner* — Darwin P Erezo
*Assistant Examiner* — Brigid K Byrd
(74) *Attorney, Agent, or Firm* — Carter, DeLuca & Farrell LLP

(57) ABSTRACT

A tissue resecting instrument includes an end effector assembly having a proximal hub housing, a retainer cap extending proximally therefrom, an elongated outer shaft extending distally from the proximal hub housing, an inner cutting shaft rotatably disposed within the elongated outer shaft, and an inner core drive assembly that includes a proximal driver and a distal driver. The distal driver is coupled to the inner cutting shaft such that rotation of the distal driver rotates the inner cutting shaft relative to the elongated outer shaft. The proximal driver is slidable relative to the distal drive between a more-proximal position wherein the proximal driver is engaged with the retainer cap to rotationally fix the proximal driver, thereby rotationally locking the inner cutting shaft, and a more-distal position wherein the proximal driver is disengaged from the retainer cap permitting rotation thereof thereby permitting rotation of the inner cutting shaft.

18 Claims, 7 Drawing Sheets

(58) Field of Classification Search
CPC ........ A61B 2017/4216; A61B 17/4241; A61B 2090/035; A61B 17/3207–2017/320791
See application file for complete search history.

(56) References Cited

U.S. PATENT DOCUMENTS 1,831,786 A 11/1931 Duncan
2,708,437 A 5/1955 Hutchins
3,297,022 A 1/1967 Wallace
3,686,706 A 8/1972 Finley
3,732,858 A * 5/1973 Banko .............. A61B 17/32002 606/107
3,734,099 A 5/1973 Bender et al.
3,791,379 A 2/1974 Storz
3,812,855 A 5/1974 Banko
3,835,842 A 9/1974 Iglesias
3,850,162 A 11/1974 Iglesias
3,945,375 A 3/1976 Banko
3,980,252 A 9/1976 Tae
3,995,619 A 12/1976 Glatzer
3,996,921 A 12/1976 Neuwirth
4,011,869 A 3/1977 Seiler, Jr.
4,108,182 A 8/1978 Hartman et al.
4,146,405 A 3/1979 Timmer et al.
4,198,958 A 4/1980 Utsugi
4,203,444 A 5/1980 Bonnell et al.
4,210,146 A 7/1980 Banko
4,246,902 A 1/1981 Martinez
4,247,180 A 1/1981 Norris
4,258,721 A 3/1981 Parent et al.
4,261,346 A 4/1981 Wettermann
4,294,234 A 10/1981 Matsuo
4,316,465 A 2/1982 Dotson, Jr.
4,369,768 A 1/1983 Vukovic
4,392,485 A 7/1983 Hiltebrandt
4,414,962 A 11/1983 Carson
4,449,538 A 5/1984 Corbitt et al.
4,493,698 A 1/1985 Wang et al.
4,517,977 A 5/1985 Frost
4,543,965 A 10/1985 Pack et al.
4,567,880 A 2/1986 Goodman
4,589,414 A 5/1986 Yoshida et al.
4,601,284 A 7/1986 Arakawa et al.
4,601,290 A 7/1986 Ffron et al.
4,606,330 A 8/1986 Bonnet
4,630,598 A 12/1986 Bonnet
4,644,952 A 2/1987 Patipa et al.
4,649,919 A 3/1987 Thimsen et al.
4,700,694 A 10/1987 Shishido
4,706,656 A 11/1987 Kuboto
4,718,291 A 1/1988 Wood et al.
4,737,142 A 4/1988 Heckele
4,749,376 A 6/1988 Kensey et al.
4,756,309 A 7/1988 Sachse et al.
4,819,635 A 4/1989 Shapiro
4,844,064 A 7/1989 Thimsen et al.
4,850,354 A 7/1989 McGurk-Burleson et al.
4,856,919 A 8/1989 Takeuchi et al.
4,867,157 A 9/1989 McGurk-Burleson et al.
4,924,851 A 5/1990 Ognier et al.
4,940,061 A 7/1990 Terwilliger et al.
4,950,278 A 8/1990 Sachse et al.
4,955,882 A 9/1990 Hakky
4,971,034 A 11/1990 Doi et al.
4,986,827 A 1/1991 Akkas et al.
4,998,527 A 3/1991 Meyer
4,998,914 A 3/1991 Wiest et al.
5,007,917 A 4/1991 Evans
5,027,792 A 7/1991 Meyer
5,037,386 A 8/1991 Marcus et al.
5,105,800 A 4/1992 Takahashi et al.
5,106,364 A 4/1992 Hayafuji et al.
5,112,299 A 5/1992 Pascaloff
5,116,868 A 5/1992 Chen et al.
5,125,910 A 6/1992 Freitas
5,133,713 A 7/1992 Huang et al.
5,152,744 A 10/1992 Krause et al.
5,158,553 A 10/1992 Berry et al.
5,163,433 A 11/1992 Kagawa et al.
5,169,397 A 12/1992 Sakashita et al.
5,176,677 A 1/1993 Wuchinich
5,195,541 A 3/1993 Obenchain
5,226,910 A 7/1993 Kajiyama et al.
5,244,459 A 9/1993 Hill
5,254,117 A 10/1993 Rigby et al.
5,269,785 A 12/1993 Bonutti
5,270,622 A 12/1993 Krause
5,275,609 A 1/1994 Pingleton et al.
5,288,290 A 2/1994 Brody
5,304,118 A 4/1994 Trese et al.
5,312,399 A 5/1994 Hakky et al.
5,312,425 A 5/1994 Evans et al.
5,312,430 A 5/1994 Rosenbluth et al.
5,320,091 A 6/1994 Grossi et al.
5,347,992 A 9/1994 Pearlman et al.
5,350,390 A 9/1994 Sher
5,364,395 A 11/1994 West, Jr.
5,374,253 A 12/1994 Burns, Sr. et al.
5,390,585 A 2/1995 Ryuh
5,392,765 A 2/1995 Muller
5,395,313 A 3/1995 Naves et al.
5,403,276 A 4/1995 Schechter et al.
5,409,013 A 4/1995 Clement
5,409,453 A 4/1995 Lundquist et al.
5,411,513 A 5/1995 Ireland et al.
5,421,819 A 6/1995 Edwards et al.
5,425,376 A 6/1995 Banys et al.
5,429,601 A 7/1995 Conley et al.
5,435,805 A 7/1995 Edwards et al.
5,443,476 A 8/1995 Shapiro
5,449,356 A 9/1995 Walbrink et al.
5,456,673 A 10/1995 Ziegler et al.
5,456,689 A 10/1995 Kresch et al.
5,483,951 A 1/1996 Frassica et al.
5,490,819 A 2/1996 Nicholas et al.
5,490,860 A 2/1996 Middle et al.
5,492,537 A 2/1996 Vancaillie
5,498,258 A 3/1996 Hakky et al.
5,501,694 A * 3/1996 Ressemann .... A61B 17/320725 606/159
5,527,331 A 6/1996 Kresch et al.
5,549,541 A 8/1996 Muller
5,556,378 A 9/1996 Storz et al.
5,563,481 A 10/1996 Krause
5,569,164 A 10/1996 Lurz
5,569,254 A 10/1996 Carlson et al.
5,569,284 A 10/1996 Young et al.
5,575,756 A 11/1996 Karasawa et al.
5,586,973 A 12/1996 Lemaire et al.
5,591,187 A 1/1997 Dekel
5,601,583 A 2/1997 Donahue et al.
5,601,603 A 2/1997 Illi
5,602,449 A 2/1997 Krause et al.
5,603,332 A 2/1997 O'Connor
5,630,798 A 5/1997 Beiser et al.
5,649,547 A 7/1997 Ritchart et al.
5,669,927 A 9/1997 Boebel et al.
5,672,945 A 9/1997 Krause
5,674,179 A 10/1997 Bonnet et al.
5,676,497 A 10/1997 Kim
5,695,448 A 12/1997 Kimura et al.
5,702,420 A 12/1997 Sterling et al.
5,709,698 A 1/1998 Adams et al.
5,730,752 A 3/1998 Alden et al.
5,733,298 A 3/1998 Berman et al.
5,741,286 A 4/1998 Recuset
5,741,287 A 4/1998 Alden et al.
5,749,885 A 5/1998 Sjostrom et al.
5,749,889 A 5/1998 Bacich et al.
5,759,185 A 6/1998 Grinberg
5,772,634 A 6/1998 Atkinson
5,775,333 A 7/1998 Burbank et al.
5,782,849 A 7/1998 Miller
5,807,240 A 9/1998 Muller et al.

(56) References Cited

U.S. PATENT DOCUMENTS

| | | | |
|---|---|---|---|
| 5,807,282 | A | 9/1998 | Fowler |
| 5,810,770 | A | 9/1998 | Chin et al. |
| 5,810,861 | A | 9/1998 | Gaber |
| 5,814,009 | A | 9/1998 | Wheatman |
| 5,833,643 | A | 11/1998 | Ross et al. |
| 5,836,868 | A | 11/1998 | Ressemann |
| 5,840,060 | A | 11/1998 | Beiser et al. |
| 5,857,995 | A | 1/1999 | Thomas et al. |
| 5,873,886 | A | 2/1999 | Larsen et al. |
| 5,899,915 | A | 5/1999 | Saadat |
| 5,911,699 | A | 6/1999 | Anis et al. |
| 5,911,722 | A | 6/1999 | Adler et al. |
| 5,913,867 | A | 6/1999 | Dion |
| 5,916,229 | A | 6/1999 | Evans |
| 5,925,055 | A | 7/1999 | Adrian et al. |
| 5,928,163 | A | 7/1999 | Roberts et al. |
| 5,944,668 | A | 8/1999 | Vancaillie et al. |
| 5,947,990 | A | 9/1999 | Smith |
| 5,951,490 | A | 9/1999 | Fowler |
| 5,956,130 | A | 9/1999 | Vancaillie et al. |
| 5,957,832 | A | 9/1999 | Taylor et al. |
| 6,001,116 | A | 12/1999 | Heisler et al. |
| 6,004,320 | A | 12/1999 | Casscells et al. |
| 6,007,513 | A | 12/1999 | Anis et al. |
| 6,024,751 | A | 2/2000 | Lovato et al. |
| 6,032,673 | A | 3/2000 | Savage et al. |
| 6,039,748 | A | 3/2000 | Savage et al. |
| 6,042,552 | A | 3/2000 | Cornier |
| 6,068,641 | A | 5/2000 | Varsseveld |
| 6,086,542 | A | 7/2000 | Glowa et al. |
| 6,090,094 | A | 7/2000 | Clifford, Jr. et al. |
| 6,090,123 | A | 7/2000 | Culp et al. |
| 6,113,594 | A | 9/2000 | Savage |
| 6,119,973 | A | 9/2000 | Galloway |
| 6,120,147 | A | 9/2000 | Vijfvinkel et al. |
| 6,120,462 | A | 9/2000 | Tibner et al. |
| 6,132,448 | A | 10/2000 | Perez et al. |
| 6,149,633 | A | 11/2000 | Maaskamp |
| 6,156,049 | A | 12/2000 | Lovato et al. |
| 6,159,160 | A | 12/2000 | Hsei et al. |
| 6,159,209 | A | 12/2000 | Hakky |
| 6,203,518 | B1 | 3/2001 | Anis et al. |
| 6,217,543 | B1 | 4/2001 | Anis et al. |
| 6,220,368 | B1 * | 4/2001 | Ark .................... A61B 17/1626 173/217 |
| 6,224,603 | B1 | 5/2001 | Marino |
| 6,244,228 | B1 | 6/2001 | Kuhn et al. |
| 6,258,111 | B1 | 7/2001 | Ross et al. |
| 6,277,096 | B1 | 8/2001 | Cortella et al. |
| 6,315,714 | B1 | 11/2001 | Akiba |
| 6,358,200 | B1 | 3/2002 | Grossi |
| 6,358,263 | B2 | 3/2002 | Mark et al. |
| 6,359,200 | B1 | 3/2002 | Day |
| 6,402,701 | B1 | 6/2002 | Kaplan et al. |
| 6,428,486 | B2 | 8/2002 | Ritchart et al. |
| 6,471,639 | B2 | 10/2002 | Rudischhauser et al. |
| 6,494,892 | B1 | 12/2002 | Ireland et al. |
| 6,585,708 | B1 | 7/2003 | Maaskamp |
| 6,610,066 | B2 | 8/2003 | Dinger et al. |
| 6,626,827 | B1 | 9/2003 | Felix et al. |
| 6,632,182 | B1 | 10/2003 | Treat |
| 6,656,132 | B1 | 12/2003 | Ouchi |
| 6,712,773 | B1 | 3/2004 | Viola |
| 6,824,544 | B2 | 11/2004 | Boebel et al. |
| 6,837,847 | B2 | 1/2005 | Ewers et al. |
| 7,025,720 | B2 | 4/2006 | Boebel et al. |
| 7,025,732 | B2 | 4/2006 | Thompson et al. |
| 7,150,713 | B2 | 12/2006 | Shener et al. |
| 7,226,459 | B2 | 6/2007 | Cesarini et al. |
| 7,249,602 | B1 | 7/2007 | Emanuel |
| 7,510,563 | B2 | 3/2009 | Cesarini et al. |
| 7,763,033 | B2 | 7/2010 | Gruber et al. |
| 7,922,737 | B1 | 4/2011 | Cesarini et al. |
| 8,025,656 | B2 | 9/2011 | Gruber et al. |
| 8,061,359 | B2 | 11/2011 | Emanuel |
| 8,062,214 | B2 | 11/2011 | Shener et al. |
| 8,419,626 | B2 | 4/2013 | Shener-Irmakoglu et al. |
| 8,465,421 | B2 | 6/2013 | Finkman et al. |
| 8,528,563 | B2 | 9/2013 | Gruber |
| 8,574,253 | B2 | 11/2013 | Gruber et al. |
| 8,647,349 | B2 | 2/2014 | Gruber et al. |
| 8,663,264 | B2 | 3/2014 | Cesarini et al. |
| 8,678,999 | B2 | 3/2014 | Isaacson |
| 8,834,487 | B2 | 9/2014 | Gruber et al. |
| 8,840,625 | B2 | 9/2014 | Adams et al. |
| 8,840,626 | B2 | 9/2014 | Adams et al. |
| 8,852,085 | B2 | 10/2014 | Shener-Irmakoglu et al. |
| 8,893,722 | B2 | 11/2014 | Emanuel |
| 8,932,208 | B2 | 1/2015 | Kendale et al. |
| 8,951,274 | B2 | 2/2015 | Adams et al. |
| 9,060,760 | B2 | 6/2015 | Sullivan et al. |
| 9,060,800 | B1 | 6/2015 | Cesarini et al. |
| 9,060,801 | B1 | 6/2015 | Cesarini et al. |
| 9,066,745 | B2 | 6/2015 | Cesarini et al. |
| 9,072,431 | B2 | 7/2015 | Adams et al. |
| 9,089,358 | B2 | 7/2015 | Emanuel |
| 9,095,366 | B2 | 8/2015 | Sullivan et al. |
| 9,125,550 | B2 | 9/2015 | Shener-Irmakoglu et al. |
| 9,155,454 | B2 | 10/2015 | Sahney et al. |
| 9,259,233 | B2 | 2/2016 | Gruber et al. |
| 9,649,125 | B2 | 5/2017 | Truckai |
| 10,363,066 | B2 | 7/2019 | Magno |
| 10,945,752 | B2 | 3/2021 | Wood et al. |
| 2002/0058958 | A1 * | 5/2002 | Walen .............. A61B 17/32002 606/170 |
| 2008/0058842 | A1 | 3/2008 | Emanuel |
| 2008/0097468 | A1 | 4/2008 | Adams et al. |
| 2008/0097469 | A1 | 4/2008 | Gruber et al. |
| 2008/0097470 | A1 | 4/2008 | Gruber |
| 2008/0097471 | A1 | 4/2008 | Adams et al. |
| 2008/0135053 | A1 | 6/2008 | Gruber et al. |
| 2008/0146872 | A1 | 6/2008 | Gruber et al. |
| 2008/0146873 | A1 | 6/2008 | Adams et al. |
| 2008/0245371 | A1 | 10/2008 | Gruber |
| 2008/0249366 | A1 | 10/2008 | Gruber et al. |
| 2008/0249534 | A1 | 10/2008 | Gruber et al. |
| 2008/0249553 | A1 | 10/2008 | Gruber et al. |
| 2008/0262308 | A1 | 10/2008 | Prestezog et al. |
| 2009/0082628 | A1 | 3/2009 | Kucklick et al. |
| 2009/0270812 | A1 | 10/2009 | Litscher et al. |
| 2009/0270895 | A1 | 10/2009 | Churchill |
| 2009/0270896 | A1 | 10/2009 | Sullivan et al. |
| 2009/0270897 | A1 | 10/2009 | Adams et al. |
| 2009/0270898 | A1 | 10/2009 | Chin et al. |
| 2010/0087798 | A1 | 4/2010 | Adams et al. |
| 2010/0152647 | A1 | 6/2010 | Shener et al. |
| 2011/0034943 | A1 | 2/2011 | Churchill et al. |
| 2011/0077674 | A1 | 3/2011 | Sullivan et al. |
| 2011/0118544 | A1 | 5/2011 | Adams et al. |
| 2011/0166419 | A1 | 7/2011 | Reif et al. |
| 2012/0067352 | A1 | 3/2012 | Gruber et al. |
| 2012/0078038 | A1 | 3/2012 | Sahney et al. |
| 2012/0172877 | A1 | 7/2012 | Ryan et al. |
| 2012/0191116 | A1 | 7/2012 | Flynn et al. |
| 2012/0259337 | A1 | 10/2012 | del Rio |
| 2013/0131452 | A1 | 5/2013 | Kuroda et al. |
| 2014/0003183 | A1 | 1/2014 | Song |
| 2014/0155923 | A1 | 6/2014 | Edwards |
| 2014/0277036 | A1 | 9/2014 | Flynn |
| 2018/0360495 | A1 | 12/2018 | Adams et al. |
| 2019/0059983 | A1 | 2/2019 | Germain et al. |

FOREIGN PATENT DOCUMENTS

| | | | |
|---|---|---|---|
| DE | 3601453 | A1 | 9/1986 |
| DE | 3615694 | A1 | 11/1987 |
| DE | 4038398 | A1 | 6/1992 |
| DE | 4440035 | A1 | 5/1996 |
| DE | 19633124 | A1 | 5/1997 |
| DE | 19751632 | C1 | 9/1999 |
| DE | 102006022827 | A1 | 12/2006 |
| EP | 0310285 | A2 | 4/1989 |
| EP | 0327410 | A1 | 8/1989 |
| EP | 0557044 | A1 | 8/1993 |

(56) References Cited

FOREIGN PATENT DOCUMENTS

| | | | |
|---|---|---|---|
| EP | 0582295 | A2 | 2/1994 |
| EP | 0606531 | A2 | 7/1994 |
| EP | 0621008 | A2 | 10/1994 |
| EP | 0806183 | A1 | 11/1997 |
| EP | 1681022 | A1 | 7/2006 |
| EP | 3275381 | A1 | 1/2018 |
| GB | 2093353 | A | 9/1982 |
| GB | 2311468 | A | 10/1997 |
| JP | 2001075416 | A | 3/2001 |
| JP | 2002529185 | A | 9/2002 |
| JP | 2002538889 | A | 11/2002 |
| JP | 2003245247 | A | 9/2003 |
| NL | 1006944 | C2 | 3/1999 |
| WO | 20198101648 | | 6/1981 |
| WO | 9211816 | A2 | 7/1992 |
| WO | 20199307821 | | 4/1993 |
| WO | 20199315664 | | 8/1993 |
| WO | 20199426181 | | 11/1994 |
| WO | 20199505777 | | 3/1995 |
| WO | 20199510981 | | 4/1995 |
| WO | 20199510982 | | 4/1995 |
| WO | 20199522935 | | 8/1995 |
| WO | 20199530377 | | 11/1995 |
| WO | 20199611638 | | 4/1996 |
| WO | 20199626676 | | 9/1996 |
| WO | 20199709922 | | 3/1997 |
| WO | 20199717027 | | 5/1997 |
| WO | 20199719642 | | 6/1997 |
| WO | 20199724071 | | 7/1997 |
| WO | 20199734534 | | 9/1997 |
| WO | 20199735522 | | 10/1997 |
| WO | 9810707 | | 3/1998 |
| WO | 20199809569 | | 3/1998 |
| WO | 20199846147 | | 10/1998 |
| WO | 20199903407 | | 1/1999 |
| WO | 20199903409 | | 1/1999 |
| WO | 20199907295 | | 2/1999 |
| WO | 20199911184 | | 3/1999 |
| WO | 20199939648 | | 8/1999 |
| WO | 20199944506 | | 9/1999 |
| WO | 20199960935 | | 12/1999 |
| WO | 0012010 | A1 | 3/2000 |
| WO | 0028890 | A1 | 5/2000 |
| WO | 0033743 | A1 | 6/2000 |
| WO | 0044295 | A1 | 8/2000 |
| WO | 0047116 | A1 | 8/2000 |
| WO | 0057797 | A1 | 10/2000 |
| WO | 0135831 | A1 | 5/2001 |
| WO | 0158368 | A1 | 8/2001 |
| WO | 0195810 | A2 | 12/2001 |
| WO | 02069808 | A2 | 9/2002 |
| WO | 03022164 | A1 | 3/2003 |
| WO | 03077767 | A1 | 9/2003 |
| WO | 2005060842 | A1 | 7/2005 |
| WO | 2005096963 | A2 | 10/2005 |
| WO | 2006105283 | A2 | 10/2006 |
| WO | 2006121968 | A2 | 11/2006 |
| WO | 2006121970 | A2 | 11/2006 |
| WO | 2007044833 | A2 | 4/2007 |
| WO | 2012044705 | A1 | 4/2012 |

* cited by examiner

TISSUE RESECTING INSTRUMENT INCLUDING A ROTATION LOCK FEATURE

CROSS-REFERENCE TO RELATED APPLICATIONS

This application is a continuation of U.S. patent application Ser. No. 16/359,484, filed on Mar. 20, 2019, now U.S. Pat. No. 10,945,752, the entire contents of which are hereby incorporated herein by reference.

BACKGROUND

1. Technical Field

The present disclosure relates generally to the field of tissue resection. In particular, the present disclosure relates to a tissue resecting instrument including a rotation lock feature.

2. Background of Related Art

Tissue resection may be performed endoscopically within an organ, such as a uterus, by inserting an endoscope (or hysteroscope) into the uterus and passing a tissue resection instrument through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is an end effector assembly of a tissue resecting instrument. The end effector assembly includes a proximal hub housing, a retainer cap fixed relative to and extending proximally from the proximal hub housing, an elongated outer shaft fixed relative to and extending distally from the proximal hub housing, an inner cutting shaft extending within and rotatable relative to the elongated outer shaft, and an inner core drive assembly extending at least partially through the retainer cap and the proximal hub housing. The inner core drive assembly includes a proximal driver configured to receive a rotational input and a distal driver rotationally fixed and slidable relative to the proximal driver. The distal driver is coupled to the inner cutting shaft such that rotation of the distal driver rotates the inner cutting shaft relative to the elongated outer shaft. The proximal driver is slidable relative to the distal drive between a more-proximal position wherein the proximal driver is engaged with the retainer cap to rotationally fix the proximal driver relative to the retainer cap, thereby rotationally locking the inner cutting shaft relative to the elongated outer shaft, and a more-distal position wherein the proximal driver is disengaged from the retainer cap to permit rotation of the proximal driver relative to the retainer cap, thereby permitting rotation of the inner cutting shaft relative to the elongated outer shaft.

In an aspect of the present disclosure, the inner core drive assembly further includes a biasing member configured to bias the proximal driver towards the more-proximal position.

In another aspect of the present disclosure, the proximal driver includes a proximally-facing cavity configured to receive and rotationally engage a driver rotor configured to provide the rotational input.

In still another aspect of the present disclosure, the proximal driver and the distal driver cooperate to define an outflow path disposed in fluid communication with an interior of the inner cutting shaft. Further, the proximal hub housing may define an outflow opening in fluid communication with the outflow path.

In yet another aspect of the present disclosure, in the more-proximal position, a tab of the proximal driver is engaged within a notch of the retainer cap to rotationally fix the proximal driver relative to the retainer cap.

In still yet another aspect of the present disclosure, the elongated outer shaft defines a window at a distal end portion thereof. In such aspects, in the more-proximal position of the proximal driver, the inner cutting shaft may be locked in a closed position relative to the elongated outer shaft wherein the inner cutting shaft blocks the window of the elongated outer shaft.

Also provided in accordance with aspects of the present disclosure is a tissue resecting instrument including a handpiece assembly and an end effector assembly. The handpiece assembly includes a handle housing, a motor disposed within the handle housing, and a drive rotor operably coupled to and extending from the motor. The end effector assembly is configured to releasably engage the handpiece assembly and includes a proximal hub housing, a retainer cap fixed relative to and extending proximally from the proximal hub housing, an elongated outer shaft fixed relative to and extending distally from the proximal hub housing, an inner cutting shaft extending within and rotatable relative to the elongated outer shaft, and an inner core drive assembly extending at least partially through the retainer cap and the proximal hub housing. The inner core drive assembly includes a proximal driver and a distal driver rotationally fixed and slidable relative to the proximal driver, the distal driver coupled to the inner cutting shaft such that rotation of the distal driver rotates the inner cutting shaft relative to the elongated outer shaft. The proximal driver is initially disposed in a more-proximal position relative to the distal driver wherein the proximal driver is engaged with the retainer cap to rotationally fix the proximal driver relative to the retainer cap, thereby rotationally locking the inner cutting shaft relative to the elongated outer shaft. During engagement of the end effector assembly with the handpiece assembly, the drive rotor is operably engaged with the proximal driver and urges the proximal driver to a more-distal position relative to the distal driver wherein the proximal driver is disengaged from the retainer cap to permit rotation of the proximal driver relative to the retainer cap, thereby permitting rotation of the inner cutting shaft relative to the elongated outer shaft.

In an aspect of the present disclosure, the inner core drive assembly further includes a biasing member configured to bias the proximal driver towards the more-proximal position. During engagement of the end effector assembly with the handpiece assembly, the drive rotor urges the proximal driver to the more-distal position against the bias of the biasing member.

In another aspect of the present disclosure, the end effector assembly includes an engagement lever extending from the proximal hub housing. The engagement lever is configured to mechanically engage the handle housing of the handpiece assembly to engage the end effector assembly with the handpiece assembly.

In another aspect of the present disclosure, the proximal driver includes a proximally-facing cavity configured to receive and rotationally engage the driver rotor therein. In such aspects, the drive rotor may be configured to bottom-out with the proximally-facing cavity and thereafter urge the proximal driver to the more-distal position during engagement of the end effector assembly with the handpiece assembly.

In still another aspect of the present disclosure, the proximal driver and the distal driver cooperate to define an outflow path disposed in fluid communication with an interior of the inner cutting shaft. In such aspects, the proximal hub housing may define an outflow opening and the handle housing may define an outflow port wherein the outflow opening and the outflow port are disposed in fluid communication with the outflow path.

In yet another aspect of the present disclosure, a tab of the proximal driver is engaged within a notch of the retainer cap to rotationally fix the proximal driver relative to the retainer cap.

In still yet another aspect of the present disclosure, the elongated outer shaft defines a window at a distal end portion thereof. In such aspects, in the more-proximal position of the proximal driver, the inner cutting shaft is locked in a closed position relative to the elongated outer shaft wherein the inner cutting shaft blocks the window of the elongated outer shaft.

In another aspect of the present disclosure, with the end effector assembly engaged with the handpiece assembly and the motor activated, the motor is configured to drive rotation of the drive rotor to thereby drive rotation of the proximal and distal drivers and, thus, the inner cutting shaft. In such aspects, upon subsequent deactivation, the motor is configured to further drive rotation of the drive rotor to thereby drive rotation of the proximal and distal drivers and the inner cutting shaft back to initial positions thereof.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1A:
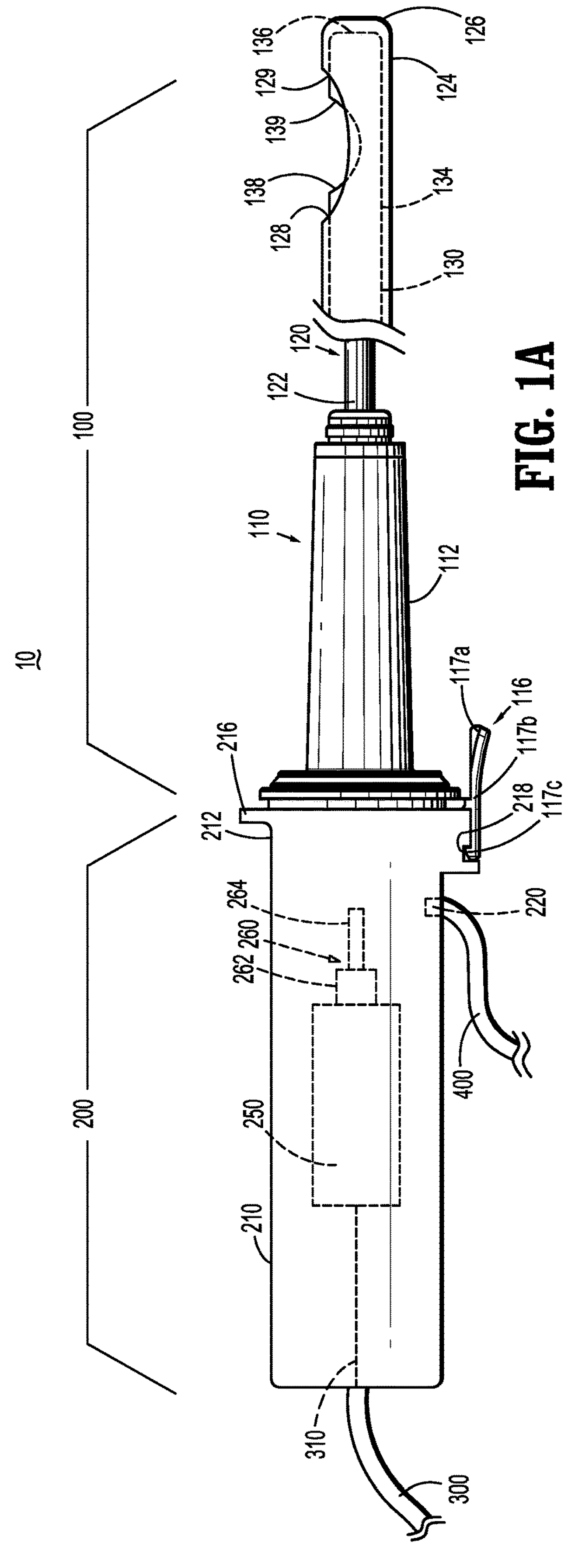
FIG. 1A is a side view of a tissue resecting instrument provided in accordance with aspects of the present disclosure including a handpiece assembly and an end effector assembly, wherein a distal end portion of the end effector assembly is enlarged to better illustrate features thereof and an inner cutting shaft of the end effector assembly is disposed in a first position.

Referring generally to FIG. 1A, a tissue resecting instrument 10 provided in accordance with the present disclosure and configured to resect tissue includes an end effector assembly 100 and a handpiece assembly 200. Tissue resecting instrument 10 is adapted to connect to a control unit (not shown) via a cable 300 to provide power and control functionality to tissue resecting instrument 10, although tissue resecting instrument 10 may alternatively or additionally include controls associated with handpiece assembly 200 and/or a power source, e.g., battery, disposed within handpiece assembly 200. Tissue resecting instrument 10 is further adapted to connect to a fluid management system (not shown) via outflow tubing 400 for applying suction to remove fluid, tissue, and debris from a surgical site via tissue resecting instrument 10, as detailed below. The control unit and fluid management system may be integral with one another, coupled to one another, or separate from one another.

Tissue resecting instrument 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In any of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for interchangeable use of different end effector assemblies, e.g., different length, configuration, etc., end effector assemblies, with handpiece assembly 200.

Continuing with reference to FIG. 1A, handpiece assembly 200 generally includes a handle housing 210, an outflow port 220 (see FIGS. 8 and 9) defined through handle housing 210, a motor 250 disposed within handle housing 210, and a drive rotor 260 disposed within handle housing 210 and operably coupled to motor 250. Handpiece assembly 200 may further include one or more controls (not shown) disposed on or operably associated with handle housing 210 to facilitate activation of tissue resecting instrument 10. Further, outflow tubing 400 is configured to connect to outflow port 220 to thereby connect outflow port 220 to the fluid management system (not shown). The fluid management system includes a vacuum source to establish suction through tissue resecting instrument 10 and outflow tubing 400 to facilitate removal of fluid, tissue, and debris from the surgical site and may also include a collection reservoir, e.g., a collection canister, for collecting the removed fluid, tissue, and debris. As an alternative or in addition to a vacuum source establishing suction through tissue resecting instrument 10 and outflow tubing 400, vacuum may be created therethrough via a pressure differential between the surgical site and the outflow path.

Handle housing 210 defines a pencil-grip configuration, although other configurations are also contemplated, e.g., pistol-grip configurations, and includes an open distal end portion 212 communicating with an internal bore 214 (FIGS. 8 and 9), and a distal hub 216 disposed about open distal end portion 212 thereof. Distal hub 216 defines an annular recess 218 configured to facilitate releasably engagement of end effector assembly 100 with handpiece assembly 200, as detailed below. Open distal end portion 212 of handle housing 210 provides access to drive rotor 260 and internal bore 214 (FIGS. 8 and 9) within handle housing 210 such that, upon engagement of end effector assembly 100 with handpiece assembly 200, as also detailed below, a portion of end effector assembly 100 extends through open distal end portion 212 and into internal bore 214 (FIGS. 8 and 9) to operably couple with drive rotor 260 and fluidly couple end effector assembly 100 with internal bore 214 (FIGS. 8 and 9) and, thus, outflow port 220.

Cable 300 extends proximally from handle housing 210 and is configured to connect to the control unit (not shown) to provide power and control functionality to tissue resecting instrument 10. Cable 300, more specifically, houses one or more wires 310 that extend into handle housing 210 and connect to the controls thereof and/or motor 250 to power motor 250 and control operation of tissue resecting instrument 10 in accordance with controls associated with handpiece assembly 200, the control unit, and/or other remote control devices, e.g., a footswitch (not shown).

Drive rotor 260 is operably coupled with and extends distally from motor 250 such that, upon activation of motor 250, motor 250 drives rotation of drive rotor 260. Drive rotor 260 defines a base 262 and rotor body 264 extending distally from base 262. At least a portion of rotor body 264 defines a non-circular cross-sectional configuration, e.g., a square or other polygonal configuration, and is configured for at least partial receipt within proximal driver 152 of end effector assembly 100 (see FIG. 9) in fixed rotational orientation relative thereto upon engagement of end effector assembly 100 with handpiece assembly 200. As such, activation of motor 250 drives rotation of drive rotor 260 to, in turn, drive proximal driver 152 of end effector assembly 100 (see FIG. 9).

Referring to FIGS. 1A-2B, end effector assembly 100 includes a proximal hub housing 110, an elongated outer shaft 120 monolithically formed, fixedly engaged, or otherwise connected with and extending distally from proximal hub housing 110, an inner cutting shaft 130 disposed within elongated outer shaft 120, a retainer cap 140 engaged about a proximal end portion of proximal hub housing 110, and an inner core drive assembly 150.

Proximal hub housing 110 of end effector assembly 100 includes a distal body portion 112 and a proximal extension portion 114 that may be monolithically formed, engaged, or otherwise connected to one another. With end effector assembly 100 engaged with handpiece assembly 200, proximal extension portion 114 of proximal hub housing 110 extends into internal bore 214 (FIGS. 8 and 9) of handle housing 210 of handpiece assembly 200 while distal body portion 112 substantially abuts and extends distally from handle housing 210 of handpiece assembly 200. Proximal extension portion 114 of proximal hub housing 110 defines an outflow opening 115 through a sidewall thereof that is configured to fluidly communicate with internal bore 214 of handle housing 210 of handpiece assembly 200 when end effector assembly 100 is engaged therewith.

An engagement lever 116 extends from proximal hub housing 110. Engagement lever 116 includes a finger tab 117*a* and an engagement tooth 117*b* disposed on opposite sides of a living hinge pivot 117*c* such that urging finger tab 117*a* towards proximal hub housing 110 urges engagement tooth 117*b* away from proximal hub housing 110, and vice versa.

Upon insertion of proximal extension portion 114 of proximal hub housing 110 of end effector assembly 100 into internal bore 214 (FIGS. 8 and 9) of handle housing 210 of handpiece assembly 200, engagement tooth 117*b* is configured to cam over distal hub 216 of handpiece assembly 200 and into engagement within annular recess 218 of distal hub 216 to engage end effector assembly 100 and handpiece assembly 200 with one another. Disengagement of end effector assembly 100 from handpiece assembly 200 is effected by depressing finger tab 117*a* towards proximal hub housing 110 to thereby withdraw engagement tooth 117*b* from annular recess 218. With engagement tooth 117*b* disengaged from annular recess 218, end effector assembly 100 may be moved distally relative to handpiece assembly 200 to withdraw proximal extension portion 114 from internal bore 214 (FIGS. 8 and 9) of handle housing 210, thereby disengaging end effector assembly 100 from handpiece assembly 200.

Figure 1B:
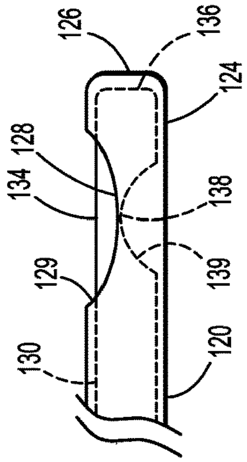
FIG. 1B is an enlarged, side view of the distal end portion of the end effector assembly of FIG. 1A wherein the inner cutting shaft is disposed in a second position.
Figure 2A:
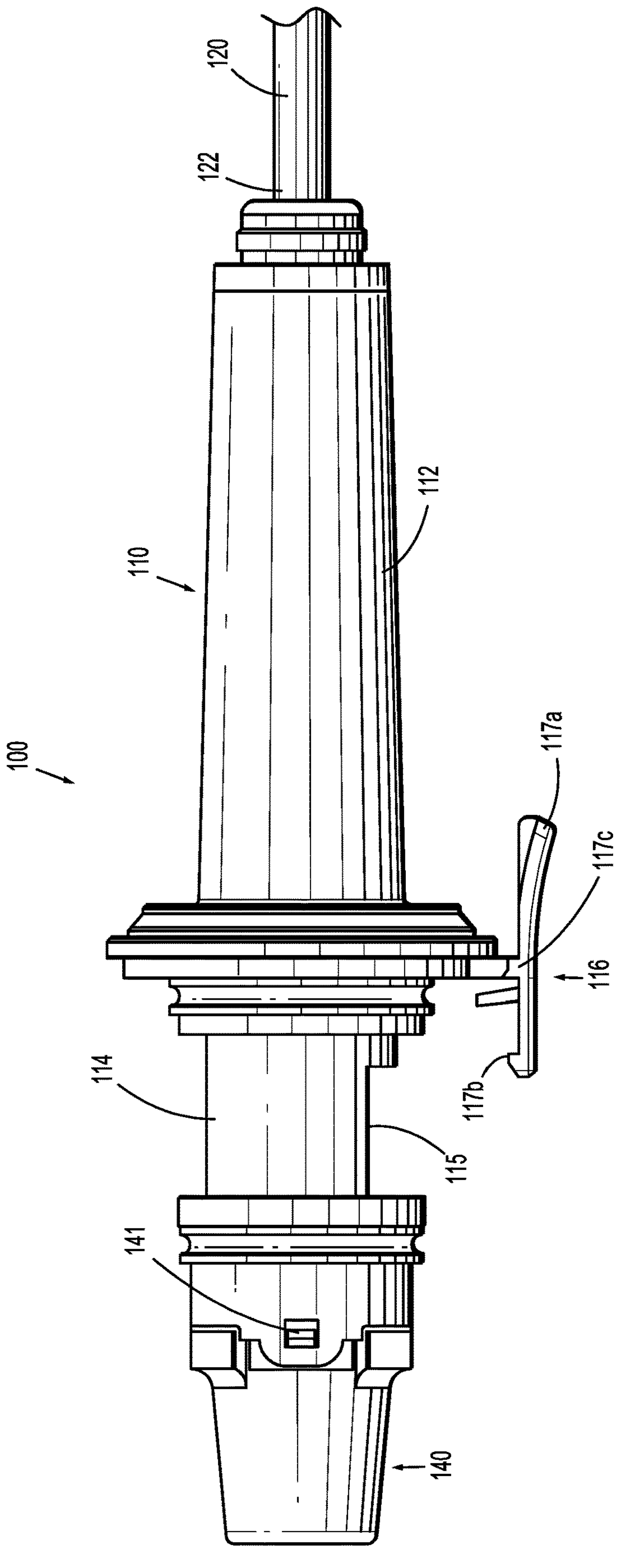
FIG. 2A is a side view of a proximal portion of the end effector assembly of FIG. 1A.
Figure 2B:
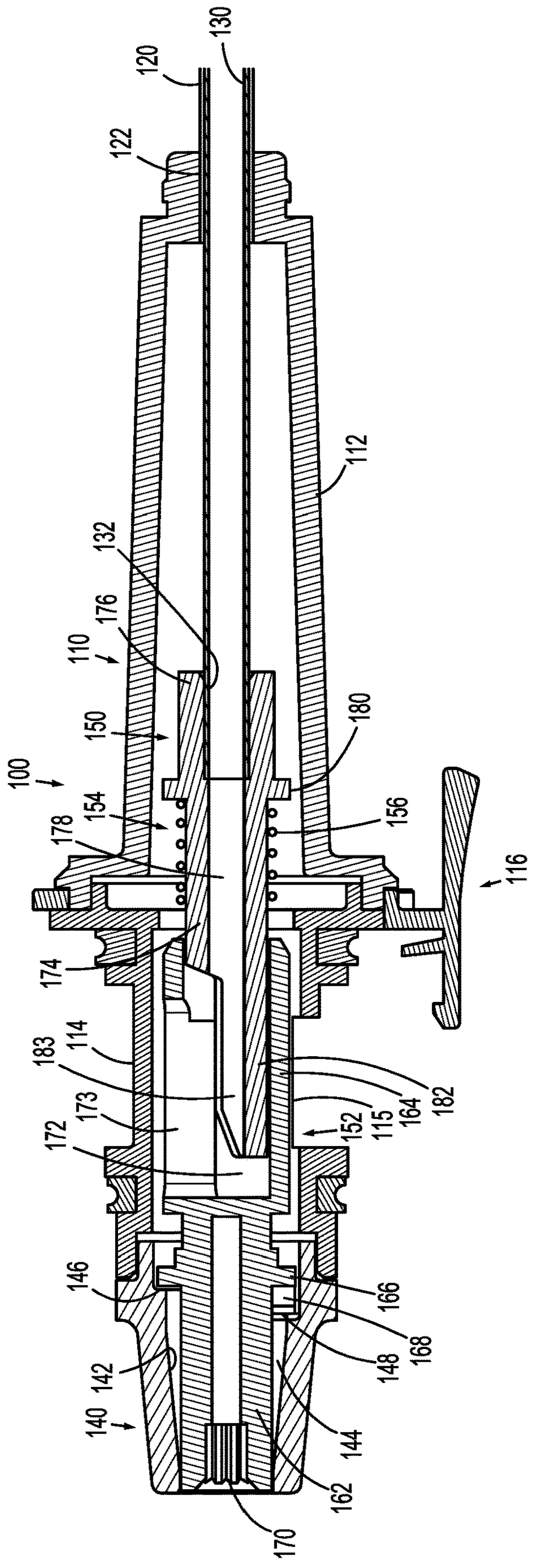
FIG. 2B is a longitudinal, cross-sectional of the proximal portion of the end effector assembly of FIG. 2A.
Figure 3:
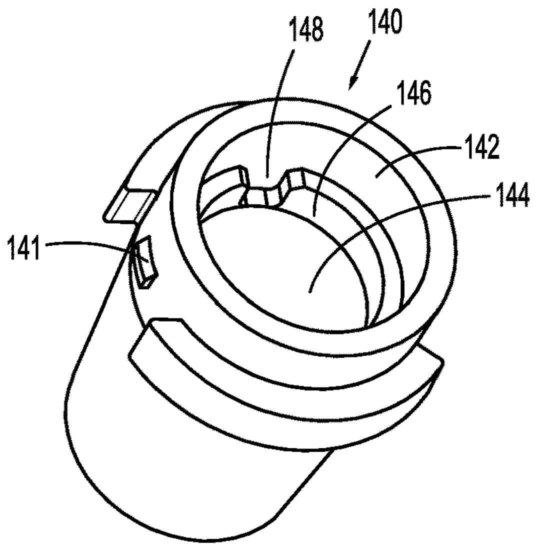
FIG. 3 is a perspective view of a retainer cap of the end effector assembly of FIG. 1A.
Figure 4:
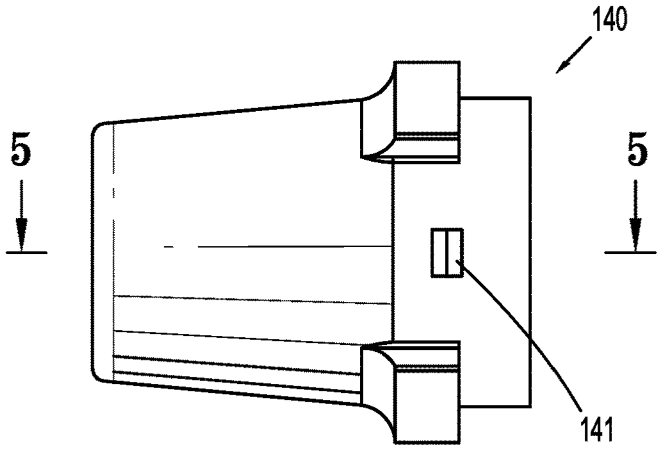
FIG. 4 is a side view of the retainer cap of FIG. 3.
Figure 5:
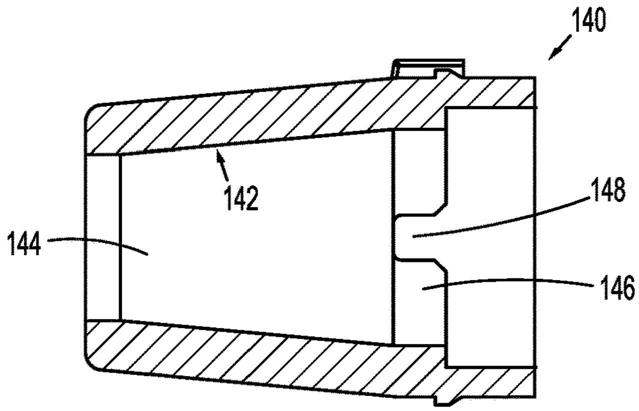
FIG. 5 is a longitudinal, cross-sectional view taken across section line "5-5" of FIG. 4.

Referring to FIGS. 1A and 1B, elongated outer shaft 120 of end effector assembly 100 includes a proximal end portion 122 fixedly engaged with distal body portion 112 of proximal hub housing 110 (see also FIG. 2B). Elongated outer shaft 120 further includes a distal end portion 124 defining a closed distal end 126 and a window 128 proximally-spaced from closed distal end 126. Window 128 provides access to the interior of elongated outer shaft 120 and may be surrounded by a cutting edge 129 about the outer perimeter of window 128 so as to facilitate cutting of tissue passing through window 128 and into elongated outer shaft 120.

Inner cutting shaft 130 of end effector assembly 100 extends through elongated outer shaft 120. Inner cutting shaft 130 defines a proximal end portion 132 (see FIG. 2B) and a distal end portion 134. Proximal end portion 132 of inner cutting shaft 130 is operably coupled with inner core drive assembly 150, as detailed below (see FIG. 2B). Distal end portion 134 of inner cutting shaft 130 defines a closed distal end 136 and a window 138 proximally-spaced from closed distal end 136. Window 138 provides access to the interior of inner cutting shaft 130 and may be surrounded by a cutting edge 139 about the outer perimeter of window 138 so as to facilitate cutting of tissue passing through window 138 and into inner cutting shaft 130.

Inner cutting shaft 130 is rotatable within and relative to elongated outer shaft 120 to thereby rotate window 138 relative to window 128. More specifically, inner cutting shaft 130 is configured to rotate such that cutting edge 139 and window 138 are exposed within window 128 of elongated outer shaft 120 during at least a portion of the rotational motion of inner cutting shaft 130 to enable cutting of tissue therewith. As detailed below, suction is provided to facilitate drawing tissue into window 128 of elongated outer shaft 120 and window 138 of inner cutting shaft 130 and, thus, to facilitate the cutting of tissue extending into inner cutting shaft 130 as inner cutting shaft 130 is rotate relative to elongated outer shaft 120. The applied suction also facilitates removal of tissue, fluids, and debris through inner cutting shaft 130, as detailed below. Other suitable configurations of elongated outer shaft 120 and/or inner cutting shaft 130 that cooperate to facilitate tissue cutting are also contemplated such as for example, both reciprocation and rotation of inner cutting shaft 130 relative to elongated outer shaft 120.

With additional reference to FIGS. 2A-5, retainer cap 140 is connected to proximal extension portion 114 of proximal hub housing 110 and extends proximally therefrom. Retainer cap 140 may be engaged with proximal extension portion 114, e.g., via snap-fit engagement of tabs 141 (FIGS. 3-5) of retainer cap 140 within corresponding slots (not shown) defined within proximal extension portion 114, may be monolithically formed with proximal extension portion 114 of proximal hub housing 110, or may be connected thereto in any other suitable manner. Retainer cap 140 includes an interior surface 142 defining a longitudinal lumen 144 extending through retainer cap 140. An internal collar 146 protrudes radially inwardly from interior surface 142 into longitudinal lumen 144. Internal collar 146 includes a distally-oriented notch 148 defined therein.

Figure 9:
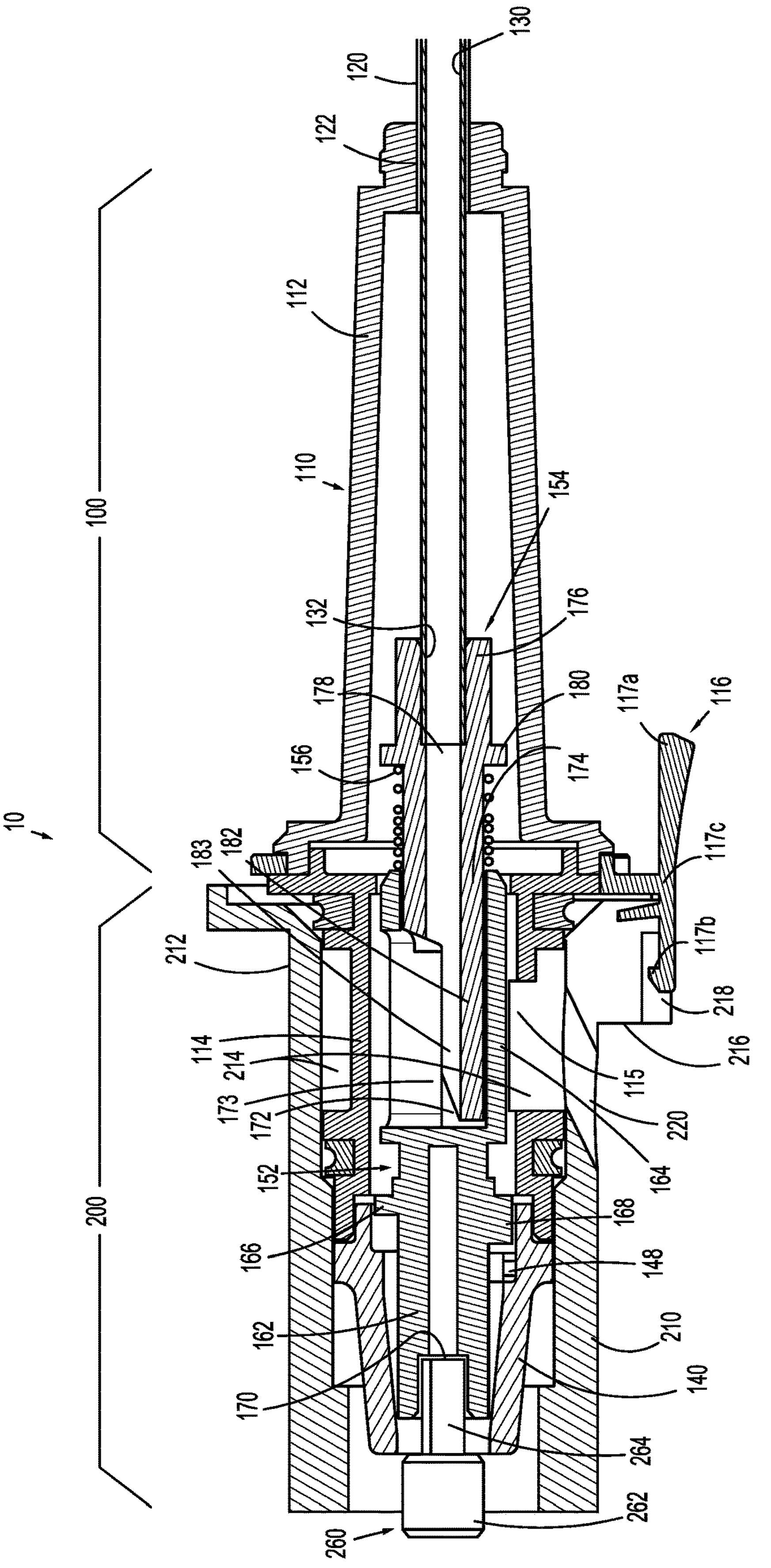
FIG. 9 is a longitudinal, cross-sectional view of the portion of the tissue resecting instrument of FIG. 8, with the end effector assembly engaged with the handpiece assembly.

Turning back to FIGS. 2A and 2B, inner core drive assembly 150 is operably disposed within at least a portion of proximal hub housing 110 and retainer cap 140 and is configured to operably couple drive rotor 260 of handpiece assembly 200 (see FIGS. 1 and 9) with inner cutting shaft 130 such that rotation of drive rotor 260 (FIGS. 1 and 9) drives rotation of inner cutting shaft 130 within and relative to elongated outer shaft 120. Inner core drive assembly 150, more specifically, includes a proximal driver 152, a distal driver 154, and a biasing member 156, e.g., a coil compression spring. In some embodiments, inner core drive assembly 150 further includes a threaded coupler and cam follower (not shown) operable to convert rotation of drive rotor 260 (FIGS. 1 and 9) into reciprocation of inner cutting shaft 130 such that inner cutting shaft 130 is both rotated and reciprocated in response to rotation of drive rotor 260 (see FIGS. 1 and 9). Additionally or alternatively, inner core drive assembly 150 may include gearing (not shown) configured to amplify or attenuate the output rotation of inner cutting shaft 130 relative to the input rotation from drive rotor 260 (FIGS. 1 and 9).

Figure 6:
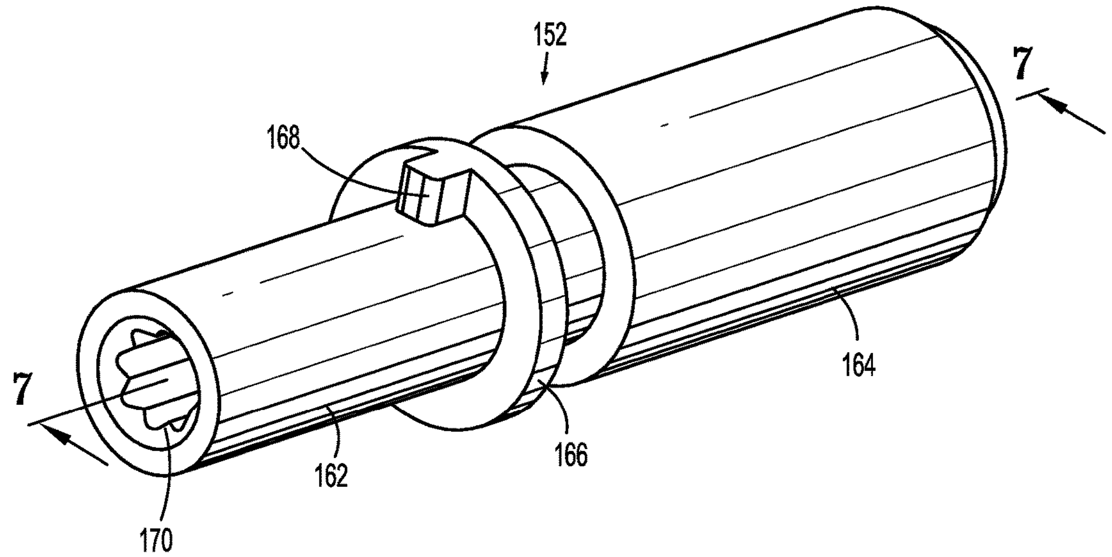
FIG. 6 is perspective view of a proximal driver of the end effector assembly of FIG. 1A.
Figure 7:
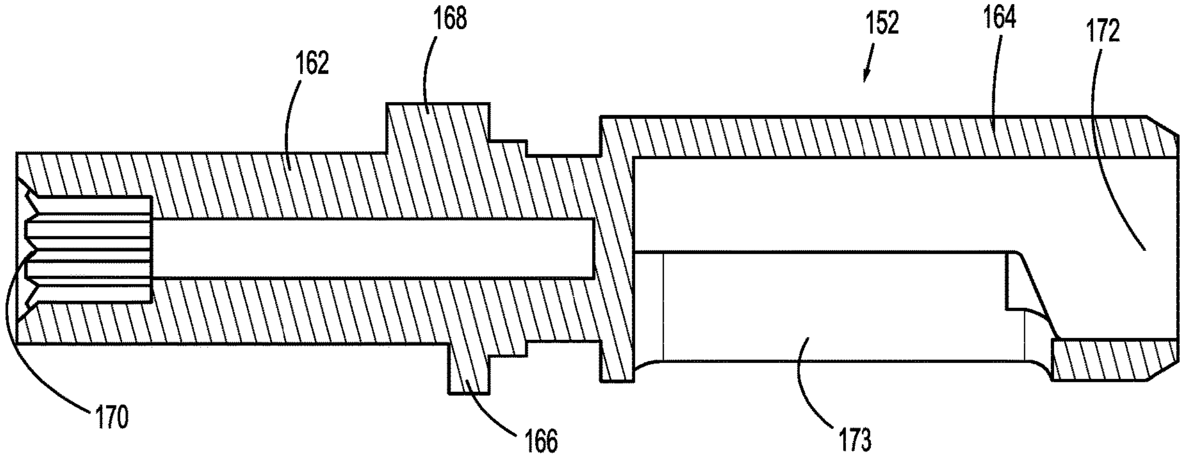
FIG. 7 is a longitudinal, cross-sectional view taken across section line "7-7" of FIG. 6.

Referring also to FIGS. 6 and 7, proximal driver 152 of inner core drive assembly 150 includes a proximal body portion 162 and a distal body portion 164 that may be monolithically formed with one another, engaged with one another, or otherwise connected to one another. Proximal body portion 162 includes an external collar 166 disposed annularly about proximal body portion 162. External collar 166 includes a proximally-oriented tab 168 that extends therefrom along the exterior surface of proximal body portion 162. Proximal body portion 162 further includes a proximally-facing cavity 170 at least a portion of which has a non-circular cross-sectional configuration, e.g., an 8-point star or other polygonal configuration, that is configured to at least partially receive drive rotor 260 of handpiece assembly 200 in fixed rotational orientation (see FIG. 9). Distal body portion 164 includes a distally-facing cavity 172 at least a portion of which has a non-circular cross-sectional configuration, e.g., a rectangular or other polygonal configuration. A longitudinally-extending slot 173 defined through a side wall of distal body portion 164 communicates with distally-facing cavity 172.

With reference to FIG. 2B, distal driver 154 of inner core drive assembly 150 includes a proximal body portion 174, a distal body portion 176, and a lumen 178 extending longitudinally through proximal and distal body portions 174, 176, respectively. Proximal and distal body portions 174, 176, respectively may be monolithically formed, engaged, or otherwise connected to one another. Distal driver 154 further includes a collar 180 disposed thereabout between proximal and distal body portions 174, 176, respectively. Distal driver 154 may be longitudinally fixed within and rotatable relative to proximal hub housing 110. In other embodiments, e.g., where distal driver 154 imparts both reciprocation and rotation to inner cutting shaft 130, distal driver 154 may be both rotatable and reciprocatable relative to proximal hub housing 110.

Proximal body portion 174 of distal driver 154 of inner core drive assembly 150 includes a proximal foot 182 extending proximally therefrom. Proximal foot 182 defines a channel 183 that communicates with lumen 178 and is open along the length of proximal foot 182. At least a portion of proximal foot 182 defines a non-circular cross-sectional configuration, e.g., a rectangular or other polygonal configuration, and is slidably received, in fixed rotational orientation, within distally-facing cavity 172 of distal body portion 164 of proximal driver 152 such that proximal and distal drivers 152, 154, respectively, are rotatably coupled to one another but slidably relative to one another. Distal body portion 164 of proximal driver 152, more specifically, is slidably disposed about proximal foot 182 and at least a portion of proximal body portion 174 of distal driver 154.

Distal body portion 176 of distal driver 154 of inner core drive assembly 150 is configured to receive and fixedly engage proximal end portion 132 of inner cutting shaft 130 therein such that the open proximal end of inner cutting shaft 130 is disposed in fluid communication with lumen 178 of distal driver 154 and such that rotation of distal driver 154 effects similar rotation of inner cutting shaft 130.

Biasing member 156 of inner core drive assembly 150 is disposed about proximal body portion 174 of distal driver 154. Biasing member 156, more specifically, is disposed about proximal body portion 174 of distal driver 154 between collar 180 and a distal end of distal body portion 164 of proximal driver 152. In this manner, biasing member 156 biases proximal driver 152 proximally such that proximally-oriented tab 168 of external collar 166 of proximal body portion 162 of proximal driver 152 is biased into engagement within distally-oriented notch 148 of internal collar 146 of retainer cap 140 to thereby rotationally fix proximal and distal drivers 152, 154 relative to retainer cap 140 and proximal hub housing 110 and, as a result, rotationally fix inner cutting blade 130 relative to elongated outer shaft 130.

Figure 8:
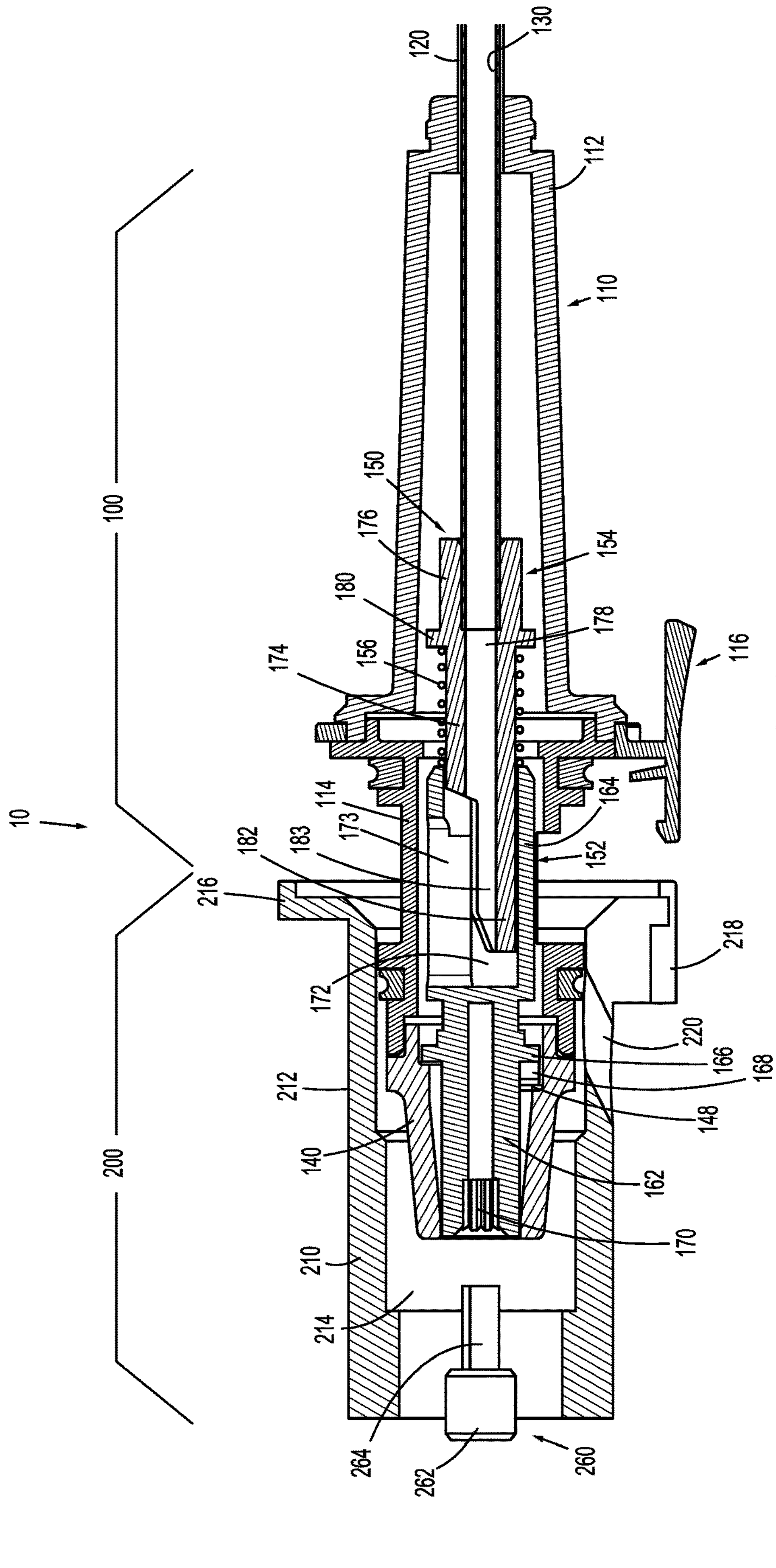
FIG. 8 is a longitudinal, cross-sectional view of a portion of the tissue resecting instrument of FIG. 1 prior to engagement of the end effector assembly with the handpiece assembly.

Turning to FIGS. 8 and 9, engagement of end effector assembly 100 with handpiece assembly 200 in preparation for use of tissue resecting instrument 10 is detailed. Initially, as noted above, prior to engagement of end effector assembly 100 with handpiece assembly 200, proximally-oriented tab 168 is engaged within distally-oriented notch 148 under the bias of biasing member 156 to rotationally fixed proximal and distal drivers 152, 154 and, thus, inner cutting shaft 130, relative to retainer cap 140 and proximal hub housing 110 and, thus, elongated outer shaft 120. Referring momentarily to FIG. 1B, end effector assembly 100 may be configured such that, in this biased, rotationally locked position, windows 128, 138 of elongated outer shaft 120 and inner cutting shaft 130, respectively, are disposed in non-overlapping orientation relative to one another, corresponding to a closed position of inner cutting shaft 130.

In order to engage end effector assembly 100 with handpiece assembly 200, end effector assembly 100, lead by retainer cap 140, is inserted proximally through open distal end portion 212 of handle housing 210 of handpiece assembly 200 and into internal bore 214 thereof, as shown in FIG. 8. Referring to FIG. 9, as end effector assembly 100 is inserted further proximally into internal bore 214, rotor body 264 is received within proximally-facing cavity 170 of proximal body portion 162 of proximal driver 152 of inner core drive assembly 150 to rotationally fix rotor body 264 within proximal driver 152 and, thus, relative to distal driver 154 and inner cutting shaft 130.

Upon further insertion of end effector assembly 100 into internal bore 214, rotor body 264 is further inserted into proximally-facing cavity 170 until rotor body 264 bottoms out within proximally-facing cavity 170. However, rotor body 264 bottoms out within proximally-facing cavity 170 prior to engagement of engagement tooth 117*b* of engagement lever 116 of end effector assembly 100 within annular recess 218 of distal hub 216 of handpiece assembly 200 and, thus, prior to engagement of end effector assembly 100 with handpiece assembly 200. Accordingly, end effector assembly 100 is required to be moved further proximally into internal bore 214 to engage end effector assembly 100 with handpiece assembly 200. As a result, with rotor body 264 bottomed-out within proximally-facing cavity 170, further proximal movement of end effector assembly 100 urges proximal driver 152 distally through and relative to retainer cap 140 and proximal hub housing 110 of end effector assembly 100.

The distal movement of proximal driver 152 under the urging from rotor body 264 is accomplished against the bias of biasing member 156. More specifically, proximal driver 152 is moved distally such that distal body portion 164 of proximal driver 152 is slid about and relative to proximal foot 182 and proximal body portion 174 of distal driver 154 to compress biasing member 156 between the distal end of distal body portion 164 of proximal driver 152 and collar 180.

In addition to compressing biasing member 156, the distal movement of proximal driver 152 relative to retainer cap 140 disengages proximally-oriented tab 168 of external collar 166 of proximal body portion 162 of proximal driver 152 from within distally-oriented notch 148 of internal collar 146 of retainer cap 140 to thereby rotationally unlock proximal and distal drivers 152, 154 relative to retainer cap 140 and proximal hub housing 110, thereby unlocking inner cutting shaft 130 from rotationally-fixed orientation, e.g., the closed position, relative to elongated outer shaft 120.

Further, at or near the insertion depth of end effector assembly 100 into handpiece assembly 200 required to rotationally unlock inner cutting shaft 130, engagement tooth 117*b* of engagement lever 116 is cammed over distal hub 216 of handpiece assembly 200 and into engagement within annular recess 218 of distal hub 216 of handpiece assembly 200 to engage end effector assembly 100 and handpiece assembly 200 with one another. Accordingly, upon engagement of end effector assembly 100 and handpiece assembly 200 with one another, inner cutting shaft 130 is rotationally unlocked.

Continuing with reference to FIG. 9, with end effector assembly 100 and handpiece assembly 200 engaged with one another, fluid communication is established between the interior of inner cutting shaft 130, lumen 178 of distal driver 154, channel 183 of proximal foot 182 of distal driver 154, distally-facing cavity 172 of proximal driver 152, longitudinally-extending slot 173 of distal body portion 164, the interior of proximal extension portion 114 of proximal hub housing 110, outflow opening 115 of proximal hub housing 110, internal bore 214 of handle housing 210, outflow port 220, and outflow tubing 400. In this manner, suction may be applied by a vacuum source of the fluid management system to which outflow tubing 400 is connected to thereby establish suction through inner cutting shaft 130 of end effector assembly 100 to suction tissue, fluids, and debris therethrough.

Referring generally to FIGS. 1A, 1B, and 9, with end effector assembly 100 engaged with handpiece assembly 200 as detailed above, tissue resecting instrument 10 is ready for use. In use, motor 250 of handpiece assembly 200 is activated to drive rotation of drive rotor 260. Upon activation of motor 250, with a head-start or delay relative to activation of motor 250, or independently thereof, suction is established through outflow tubing 400 and, thus, through tissue resecting instrument 10, e.g., via activating the vacuum source of the fluid management system.

Activation of motor 250 drives rotation of drive rotor 260 which, in turn, drives rotation of proximal driver 152 to, in turn, drive rotation of distal driver 154 and thereby rotate inner cutting shaft 130 relative to elongated outer shaft 120. The rotation of inner cutting shaft 130 relative to elongated outer shaft 120, together with the suction applied through inner cutting shaft 130, enables tissue to be drawn through cutting windows 128 and 138 and into inner cutting shaft 130, cut, and suctioned, along with fluids and debris, proximally through tissue resecting instrument 10 and outflow tubing 400 to the collection reservoir of the fluid management system.

Upon engagement of end effector assembly 100 with handpiece assembly 200, the rotational position of inner cutting shaft 130 relative to elongated outer shaft 120 is known, e.g., the closed position of inner cutting shaft 130. This is because of the rotational lock provided prior to engagement of end effector assembly 100 with handpiece assembly 200. Accordingly, upon engagement, a control program (not shown) associated with motor 250 may record the rotational position of drive rotor 260 as a home position and, after activation, ensure that drive rotor 260 stops at a rotational position corresponding to the closed position of inner cutting shaft 130 relative to elongated outer shaft 120.

The control program may utilize correlation information correlating, for example, rotation of drive rotor 260 with rotation of inner cutting shaft 130 to ensure that inner cutting shaft 130 is returned to the closed position relative to elongated outer shaft 120 after each activation. As the correlation information may vary depending upon the particular end effector assembly 100 utilized, the control program may communicate with or read information from end effector assembly 100 in order to correlate rotation of drive rotor 260 with rotation of inner cutting shaft 130 and, thus, set the home position.

Returning to the home position, corresponding to the closed position of inner cutting shaft 130, also returns proximal driver 152 to its initial rotational position whereby proximally-oriented tab 168 of external collar 166 of proximal body portion 162 of proximal driver 152 is rotationally aligned with distally-oriented notch 148 of internal collar 146 of retainer cap 140. As such, upon disengagement and withdrawal of end effector assembly 100 from handpiece assembly 200, biasing member 156 returns proximal driver 152 distally to thereby bias proximally-oriented tab 168 into engagement within distally-oriented notch 148. With tab 168 engaged within notch 148, the rotational lock is re-engaged, rotationally fixing proximal and distal drivers 152, 154, respectively, relative to retainer cap 140 and proximal hub housing 110 and, thus, rotationally locking inner cutting shaft 130 in the closed position relative to elongated outer shaft 120.

Referring generally to FIG. 1A, as an alternative to handpiece assembly 200 configured for manual grasping and manipulation during use, tissue resecting instrument 10 may alternatively be configured for use with a robotic surgical system wherein handle housing 210 is configured to engage a robotic arm of the robotic surgical system. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely controls the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly of a tissue resecting instrument, the end effector assembly comprising:
- a proximal hub housing;
- an elongated outer shaft fixed relative to and extending distally from the proximal hub housing;
- an inner cutter extending within and rotatable relative to the elongated outer shaft;
- a proximal driver configured to receive a rotational input;
- a distal driver rotationally fixed and longitudinally slidable relative to the proximal driver, the distal driver coupled to the inner cutter such that rotation of the distal driver, in response to the rotational input to the proximal driver to rotate the proximal driver, rotates the inner cutter relative to the elongated outer shaft; and
- a biasing member configured to provide a longitudinal bias to at least one of the proximal driver or the distal driver relative to the other of the proximal driver or the distal driver,
- wherein the biasing member is configured to bias the proximal driver towards a locked position, and
- wherein the proximal driver is rotationally locked relative to the proximal hub housing, thereby rotationally locking the inner cutter relative to the outer shaft.

2. The end effector assembly according to claim 1, wherein the biasing member longitudinally biases the proximal driver relative to the distal driver.

3. The end effector assembly according to claim 2, wherein the biasing member longitudinally biases the proximal driver proximally relative to the distal driver.

4. The end effector assembly according to claim 1, wherein at least one of the proximal driver or the distal driver is longitudinally slidable relative to the other between a more-overlapping position and a less-overlapping position.

5. The end effector assembly according to claim 4, wherein the biasing member is configured to bias the at least one of the proximal driver or the distal driver towards the less-overlapping position.

6. The end effector assembly according to claim 1, wherein the proximal driver is longitudinally slidable against the bias of the biasing member to an unlocked position permitting rotation of the proximal driver relative to the proximal hub housing.

7. The end effector assembly according to claim 6, wherein, in the locked position, the proximal driver is engaged with the proximal hub housing via engagement of a tab within a notch, and wherein, in the unlocked position, the tab is displaced from the notch to disengage the proximal driver from the proximal hub housing.

8. The end effector assembly according to claim 1, wherein the proximal driver and the distal driver cooperate to define an outflow path disposed in fluid communication with an interior of the inner cutter.

9. The end effector assembly according to claim 8, wherein the proximal hub housing defines an outflow opening in fluid communication with the outflow path.

10. A tissue resecting instrument, comprising:
- a handpiece assembly including a handle housing, a motor disposed within the handle housing, and a drive rotor operably coupled to and extending from the motor; and
- an end effector assembly configured to releasably engage the handpiece assembly, the end effector assembly including:
  - a proximal hub housing configured to releasably engage the handle housing;
  - an elongated outer shaft fixed relative to and extending distally from the proximal hub housing;
  - an inner cutter extending within and rotatable relative to the elongated outer shaft;
  - a proximal driver configured to operably couple to the drive rotor upon engagement of the proximal hub housing with the handle housing, the proximal driver configured to receive a rotational input from the drive rotor when operably coupled thereto;

a distal driver rotationally fixed and longitudinally slidable relative to the proximal driver, the distal driver coupled to the inner cutter such that rotation of the distal driver, in response to the rotational input to the proximal driver to rotate the proximal driver, rotates the inner cutter relative to the elongated outer shaft; and a biasing member configured to provide a longitudinal bias to at least one of the proximal driver or the distal driver relative to the other of the proximal driver or the distal driver, wherein, upon engagement of the end effector assembly with the handpiece assembly, the drive rotor is configured to urge the at least one of the proximal driver or the distal driver to longitudinally translate against the biasing of the biasing member, wherein the biasing member is configured to bias the proximal driver towards a locked position, and wherein the proximal driver is rotationally locked relative to the proximal hub housing, thereby rotationally locking the inner cutter relative to the outer shaft.

11. The tissue resecting instrument according to claim 10, wherein the biasing member longitudinally biases the proximal driver relative to the distal driver.

12. The tissue resecting instrument according to claim 11, wherein the biasing member longitudinally biases the proximal driver proximally relative to the distal driver and wherein the drive rotor is configured to urge the proximal driver distally against the bias of the biasing member upon engagement of the end effector assembly with the handpiece assembly.

13. The tissue resecting instrument according to claim 10, wherein at least one of the proximal driver or the distal driver is longitudinally slidable relative to the other between a more-overlapping position and a less-overlapping position.

14. The tissue resecting instrument according to claim 13, wherein the biasing member is configured to bias the at least one of the proximal driver or the distal driver towards the less-overlapping position.

15. The tissue resecting instrument according to claim 10, wherein the proximal driver is longitudinally slidable, under urging of the drive rotor upon engagement of the end effector assembly with the handpiece assembly, against the bias of the biasing member to an unlocked position permitting rotation of the proximal driver relative to the proximal hub housing.

16. The tissue resecting instrument according to claim 15, wherein, in the locked position, the proximal driver is engaged with the proximal hub housing via engagement of a tab within a notch, and wherein, in the unlocked position, the tab is displaced from the notch to disengage the proximal driver from the proximal hub housing.

17. The tissue resecting instrument according to claim 10, wherein the proximal driver and the distal driver cooperate to define an outflow path disposed in fluid communication with an interior of the inner cutter.

18. The tissue resecting instrument according to claim 17, wherein the proximal hub housing defines an outflow opening in fluid communication with the outflow path.

* * * * *